United States Patent
Kalhapure et al.

(10) Patent No.: US 11,433,084 B2
(45) Date of Patent: Sep. 6, 2022

(54) PREPARATION OF MICROPARTICULATE METHYLPREDNISOLONE ACETATE SUSPENSION

(71) Applicant: Somerset Therapeutics LLC, Hollywood, FL (US)

(72) Inventors: Rahul Kalhapure, Somerset, NJ (US); Prem Sagar Akasapu, Somerset, NJ (US); Veerappan Subramanian, Somerset, NJ (US); Ilango Subramanian, Somerset, NJ (US)

(73) Assignee: Somerset Therapeutics LLC, Hollywood, FL (US)

( * ) Notice: Subject to any disclaimer, the term of this patent is extended or adjusted under 35 U.S.C. 154(b) by 0 days.

(21) Appl. No.: 16/791,763

(22) Filed: Feb. 14, 2020

(65) Prior Publication Data
US 2021/0252019 A1     Aug. 19, 2021

(51) Int. Cl.
*A61K 31/573*     (2006.01)
*A61K 9/00*       (2006.01)
*A61K 47/26*      (2006.01)

(52) U.S. Cl.
CPC .......... *A61K 31/573* (2013.01); *A61K 9/0019* (2013.01); *A61K 47/26* (2013.01)

(58) Field of Classification Search
CPC .................................................. A61K 31/573
See application file for complete search history.

(56) References Cited

U.S. PATENT DOCUMENTS

2007/0178051 A1* 8/2007 Pruitt et al. .......... A61K 31/573
424/46

FOREIGN PATENT DOCUMENTS

| CN | 104706578 A | * | 6/2015 | ............. A61K 47/02 |
| WO | WO2012040229 A1 | * | 3/2012 | ............... A61K 9/14 |

OTHER PUBLICATIONS

Pfizer, Depo-Medrol, "http://labeling.pfizer.com/showlabeling.aspx?format=PDF&id=551", Jul. 2018 (Year: 2018).*
Alam et al., Formulation and evaluation of pharmaceutically equivalent parenteral depot suspension of methyl prednisolone acetate, "https://www.ncbi.nlm.nih.gov/pmc/articles/PMC2810044/", Jan. 2009 (Year: 2009).*
CN104706578A, Google English Translation, downloaded in Mar. 2021 (Year: 2021).*
Solumedrol/LPD/PK-14, Pfizer Pakistan Limited, last update date: Jan. 3, 2018 (Year: 2018).*
Pfizer, Depo-Medrol (methylprednisolone acetate injectable), Pfizer Medical Information, publication date: May 3, 2018 (Year: 2018).*

* cited by examiner

*Primary Examiner* — Mark V Stevens
*Assistant Examiner* — Alparslan Asan
(74) *Attorney, Agent, or Firm* — William D. Hare, Esq.; McNeely, Hare & War, LLP

(57) ABSTRACT

The present invention relates to a process for preparation of a water-insoluble steroid composition by moist heat sterilization. The invention particularly relates to a process for preparation of a water-insoluble steroid composition comprising moist heat sterilization or autoclaving of an aqueous slurry of methylprednisolone acetate in the presence of a specified quantity of polysorbate. The suspensions prepared by using the current invention exhibited good physical and chemical stability. Compositions related thereto are also disclosed.

14 Claims, 2 Drawing Sheets

PREPARATION OF MICROPARTICULATE METHYLPREDNISOLONE ACETATE SUSPENSION

FIELD OF THE INVENTION

Disclosed herein are processes for the preparation of a water-insoluble steroid suspension, particularly a process for making a methylprednisolone acetate suspension that includes moist heat sterilization. The present invention also relates to water-insoluble steroid suspension compositions suitable for parenteral administration.

BACKGROUND OF THE INVENTION

Methylprednisolone acetate is a synthetic glucocorticoid corticosteroid with anti-inflammatory action. Methylprednisolone acetate is pregna-1, 4-diene-3, 20-dione, 21-(acetyloxy)-11, 17-dihydroxy-6-methyl-, (6α, 11β)—and has a molecular weight of 416.51. Its structural formula is:

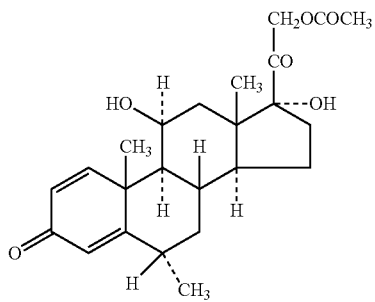

Methylprednisolone acetate suspension injection is approved as 20 mg/ml, 40 mg/mL and 80 mg/mL strengths under the brand name Depo-Medrol® by Pharmacia & Upjohn with routes of administration of intramuscular, intraarticular, soft tissue and intralesional injection. Methylprednisolone acetate suspension administered intra-muscularly is indicated for allergy, dermatologic, endocrine, gastrointestinal, hematologic, neoplastic, nervous, ophthalmic, renal, respiratory, rheumatic and other miscellaneous disease or disorders. Methylprednisolone acetate suspension administered intra-articularly or in soft tissue is indicated as an adjunctive therapy for short-term administration (to tide the patient over an acute episode or exacerbation) in acute gouty arthritis, acute and subacute bursitis, acute nonspecific tenosynovitis, epicondylitis, rheumatoid arthritis, and synovitis of osteoarthritis. Methylprednisolone acetate suspension administered intralesionally is indicated in alopecia areata, discoid lupus erythematosus; keloids, localized hypertrophic, infiltrated inflammatory lesions of granuloma annulare, lichen planus, lichen simplex chronicus (neurodermatitis) and psoriatic plaques; necrobiosis lipoidica diabeticorum.

A pharmaceutical suspension is a coarse dispersion in which insoluble solid particles are dispersed in a liquid medium. Suspensions contribute to pharmacy and medicine by supplying insoluble and often distasteful substances in a form that is pleasant to the taste, by providing a suitable form for the application of dermatological materials to the skin and sometimes to the mucous membranes, and for the parenteral administration of insoluble drugs. Therefore, pharmaceutical suspensions may be classified into three groups: orally administered mixtures, externally applied lotions and injectable preparations.

Injectable suspension formulations are administered by intravenous (IV), subcutaneous (SC) or intramuscular (IM) routes. Parenteral suspensions are heterogeneous systems that typically consist of a solid phase dispersed in a liquid phase, the liquid phase being aqueous or nonaqueous. To be effective and pharmaceutically acceptable, injectable suspensions should preferably be sterile, stable, resuspendable, syringeable, injectable, isotonic and nonirritating.

A pharmaceutical suspension preparation possesses certain desirable qualities, including the following: i) the suspended material should not settle rapidly; ii) the particles that do settle to the bottom of the container must not form a hard cake but should be readily re-dispersed into a uniform mixture when the container is shaken; and iii) the suspension must not be too viscous to pour freely from the orifice of the bottle or to flow through a syringe needle.

It is important that the characteristics of the dispersed phase are chosen with care so as to produce a suspension having optimum physical, chemical and pharmacological properties. Particle size distribution, specific surface area, inhibition of crystal growth, and changes in the polymorphic form are of special significance and the formulator must ensure that these and other properties do not change sufficiently during storage to adversely affect the performance of the suspensions with aging.

The foregoing characteristics result in manufacturing, storage, and usage requirements that make injectable suspensions one of the most difficult dosage forms to develop.

In the field of injectable preparations, aqueous suspensions for parenteral administration have already been described in scientific and patent literature. These suspensions have been known for a long time and are routinely heat sterilized as ultrafiltration sterilization is not a good option, however, autoclave sterilization could result in degradation of the drug.

U.S. Pat. No. 3,962,430 A discloses an autoclaving method for sterilization of active pharmaceutical ingredients in the presence of sodium chloride. This method has been reported to eliminate the problem of change in particle size of dexamethasone acetate, lidocaine hydrochloride, hydrocortisone alcohol, prednisolone tertiary butyl acetate, indomethacin, thiabendazole, testosterone and estradiol.

U.S. Pat. No. 6,495,534 B2 discloses the preparation of stable aqueous suspensions of medroxyprogesterone acetate in a method that utilizes steam sterilization of an aqueous solution of excipients, followed by dispersion of the drug, followed by further homogenization and aseptic filling into the final containers.

U.S. Pat. No. 7,892,483 B2 discloses a process for the sterilization of a steroid that involves heat treating the steroid in the form of a wet mass consisting essentially of the steroid, water and surfactant.

PCT Application Number WO 1999/061001A1 discloses compositions of submicron to micron sized particles of water-insoluble biologically active substances that are stabilized by thermoprotecting agents, and can be terminally steam sterilized without any significant increase of mean particle size.

U.S. Patent Publication Number 2006/0094700 A1 discloses a process for sterilizing a water-insoluble steroid composition comprising heat sterilizing the steroid in the presence of phosphate. The '700 patent publication discloses that the results of the examples show that phosphate salts have an effect on particle size during autoclaving. The phosphate salts decrease the particle size, which the inventors state may be due to the breakup of some crystal aggregates, which is important for injectable suspensions where larger particles sediment rapidly and can contribute to blockage of the fine gauge needle.

U.S. Patent Publication Number 2019/0269616 A1 discloses terminal sterilization of a methylprednisolone acetate parenteral suspension by autoclaving at 121° C. for 45 minutes.

Results reported in the patent publication show that there were no changes in methylprednisolone acetate assay values and impurities were not more than 2%, however, there was no information provided on the effect of autoclaving exposure on particle size of methylprednisolone acetate.

Thus, there exists an enduring need to develop a robust method for sterilizing parenteral suspension formulations having one or more water insoluble components, and which will provide an alternative to existing formulations. The inventors of the present invention have developed a process for preparing a methylprednisolone acetate injectable suspension by moist heat sterilization or autoclaving of an aqueous slurry of methylprednisolone acetate in the presence of a specified quantity of polysorbate. The suspensions prepared by using the current invention exhibited good physical and chemical stability.

SUMMARY OF THE INVENTION

The present invention provides a process for preparation of sterilized injectable suspensions by moist heat sterilization. Particularly, the invention relates to a process for sterilizing a water-insoluble steroid suspension comprising moist heat sterilization or autoclaving an aqueous slurry of methylprednisolone acetate in the presence of a specified quantity of polysorbate.

In another general aspect, there is provided a process for preparation of a sterilized injectable water-insoluble steroid suspension by moist heat sterilization.

In another general aspect, there is provided a process for sterilizing a water-insoluble steroid suspension comprising moist heat sterilization or autoclaving an aqueous slurry of water-insoluble steroid in the presence of polysorbate.

In another general aspect, there is provided a process for sterilizing a water-insoluble steroid suspension comprising moist heat sterilization or autoclaving an aqueous slurry of methylprednisolone acetate in the presence of polysorbate.

In another general aspect, there is provided a process for sterilizing a methylprednisolone acetate suspension comprising moist heat sterilization or autoclaving an aqueous slurry of methylprednisolone acetate in the presence of polysorbate 80 under nitrogen atmosphere.

In one general aspect, there is provided a process for preparing a sterilized injectable methylprednisolone acetate suspension, wherein the particle size of the methylprednisolone acetate in the suspension ranges from about 0.1 µm to about 30 µm.

In one general aspect, there is provided a process for preparing a sterilized injectable methylprednisolone acetate suspension, wherein the concentration of methylprednisolone acetate in a slurry can vary from about 2% to 25%, or about 5% to about 20%.

In one general aspect, there is provided a process for preparing a sterilized injectable methylprednisolone acetate suspension, wherein the dissolution profile of the suspension is identical to the reference product.

In one general aspect, there is provided a sterilized injectable suspension composition comprising a water insoluble steroid drug and one or more pharmaceutically acceptable excipients.

In one general aspect, there is provided a sterilized injectable suspension comprising about 2% to about 8% methylprednisolone acetate, about 2.82% to about 2.95% polyethylene glycol, about 0.05% to about 0.5% polysorbate 80, and one or more other pharmaceutically acceptable excipients.

In one general aspect, there is provided a process for preparation of a sterilized injectable suspension composition comprising methylprednisolone acetate and unit package formulation of the same.

In one general aspect, there is provided a process for preparation of a sterilized injectable suspension composition comprising methylprednisolone acetate and pharmaceutically acceptable excipients comprising the following steps:

a) In a suitable container dissolve polysorbate in water for injection, add the required quantity of methylprednisolone acetate to form a slurry, sterilize at a temperature of about 115° C. to about 128° C., more particularly about 122° C., for an appropriate time under nitrogen atmosphere and allow to cool, b) In a second container, dispense water and dissolve the formulation excipient in the following order: i) benzyl alcohol, ii) polyethylene glycol 3350, iii) monobasic sodium phosphate monohydrate, iv) dibasic sodium phosphate dihydrate, and v) sodium chloride, filter and make up the final volume with water and transfer it to the suspension of step (a), and c) Transfer the obtained suspension of step (b) to a sterile holding container for filling into vials of the required volume.

In another general aspect, there is provided a process for preparing a sterilized injectable methylprednisolone acetate suspension. The suspension is characterized in that the dosage form retains at least 90% w/w of the potency of methylprednisolone acetate when stored at 25° C. and 60% relative humidity or at 40° C. and 75% relative humidity for 3 months.

In another general aspect, there is provided a process for preparing a sterilized injectable methylprednisolone acetate suspension, wherein the process is capable of (i) controlling the particle size of the methylprednisolone acetate in a suspension to obtain the desired dissolution profile; (ii) making methylprednisolone acetate suspensions with variable particle size distributions by varying autoclaving exposure times; and (iii) preventing the hydrolytic degradation of methylprednisolone acetate to methylprednisolone.

In another general aspect, there is provided a process for preparing a sterilized injectable methylprednisolone acetate suspension, wherein the obtained suspension is aseptically distributed into single dose or multidose containers.

In another general aspect, there is provided a process for preparing a sterilized injectable methylprednisolone acetate suspension, wherein the obtained suspension can be easily resuspended and easily flows through a syringe needle for intradermal, subcutaneous and intramuscular administration.

In another general aspect, there is provided a process for preparing a sterilized injectable methylprednisolone acetate suspension, wherein the obtained suspension exhibits good stability throughout the shelf life as the impurities observed are well below the specified limits.

BRIEF DESCRIPTION OF THE DRAWING FIGURES

DETAILED DESCRIPTION OF THE INVENTION

Figure 1:
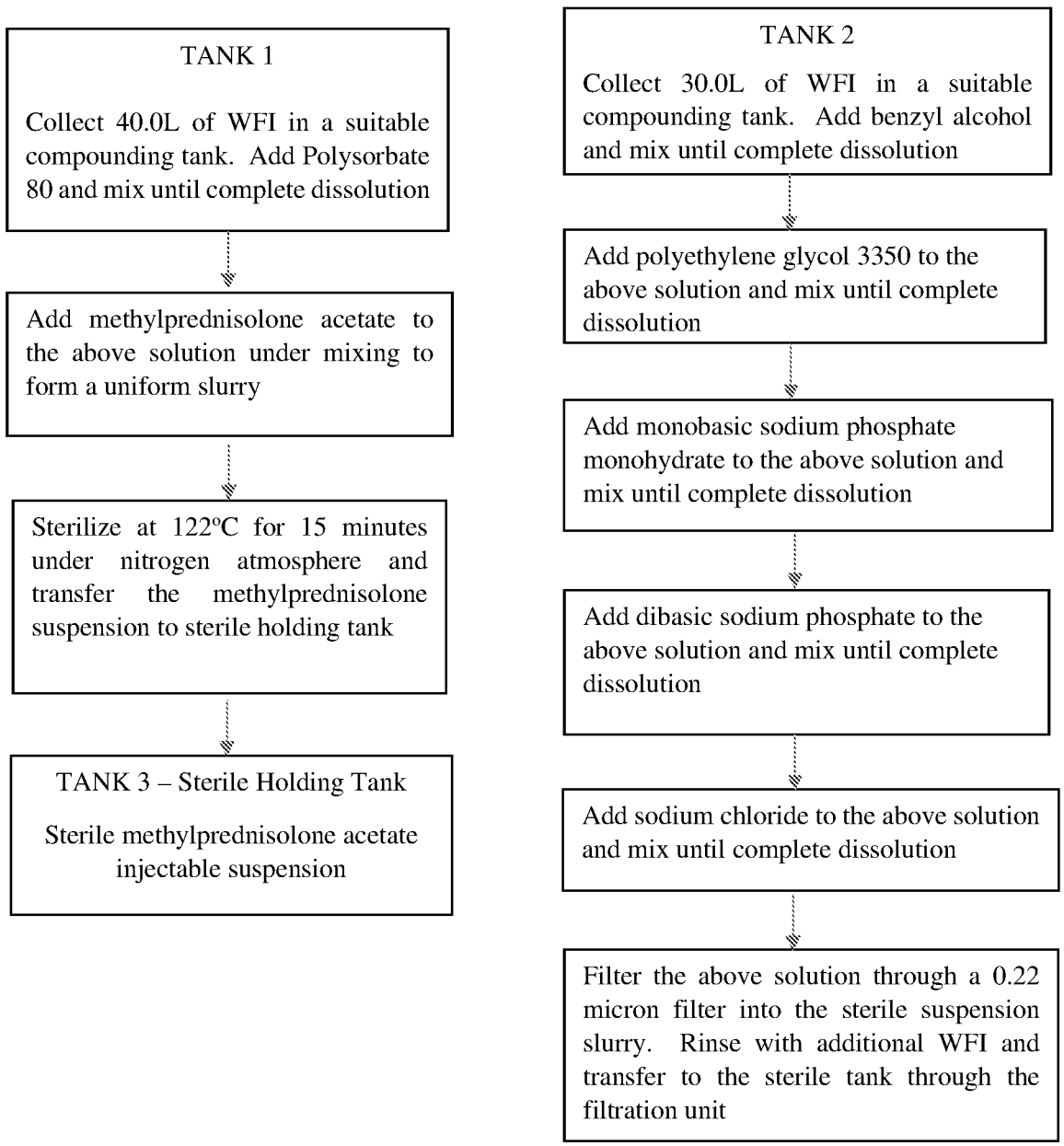
FIG. 1 is a flow chart representation of the manufacturing process for a Methylprednisolone Acetate Injectable Suspension.

The present invention provides a process for preparation of a sterilized injectable suspension using moist heat sterilization. In particular, the invention relates to a process for sterilizing a water-insoluble steroid composition comprising moist heat sterilization of an aqueous slurry of a water-insoluble steroid in the presence of polysorbate.

The term "water-insoluble steroid" is a steroid which is not completely dissolved at the concentration at which it is administered in an aqueous composition. Thus, depending upon the use and concentration, a steroid may be considered water-insoluble in one situation but not water-insoluble in another situation. While not intending to limit the scope of the invention in any way, the water-insoluble steroid referred to in the present invention relates to the pharmaceutically active agents or their pharmaceutically acceptable salts suitable for parenteral use and or normally supplied as suspension formulation. Such active agents include triamcinolone acetonide, methyl prednisolone, cortisone, cortisone acetate, dexamethasone, dexamethasone acetate, dexamethasone tertiary butyl acetate, hydrocortisone acetate, prednisolone acetate, betamethasone acetate, betamethasone, fluticasone propionate, budesonide, tipredane, dexamethasone, beclomethasone diproprionate, prednisolone, flucinolone, mometasone furoate, rofleponide palmitate, flumethasone, flunisolide, ciclesonide, deflazacort and cortivazol.

Often steroids are administered as ester, acetal, or ketal prodrugs, many of which are water-insoluble. These prodrugs are also considered to be steroids.

A "prodrug", as generally understood in the art, is a compound which is converted to a therapeutically active compound in vivo after administration, and the term should be interpreted as broadly herein as is generally understood in the art. While not intending to limit the scope of the invention, conversion may occur by hydrolysis of an ester group or some other biologically labile group.

While not intending to limit the scope of the invention in any way, methylprednisolone acetate is the preferred water-insoluble steroid composition prepared according to present invention.

The amount of methylprednisolone acetate used in the suspension is about 2% to about 10% by weight.

The compositions include the water insoluble steroid suitable for parenteral administration and one or more pharmaceutically acceptable excipients selected from the group consisting of suspending agents, tonicity agents, preservatives, surfactants, buffering agents and vehicle.

Exemplary surfactants include, but are not limited to, polyoxyethylene (20) sorbitan monooleate (polysorbate 80), polyoxyethylene (20) sorbitan monolaurate (polysorbate 20), polyoxyethylene (20) sorbitan monostearate (polysorbate 60), polyoxyl 40 stearate, polyoxyethylene 50 stearate, sodium lauryl sulfate, and the like. The term surfactants as used herein is interchangeable with wetting agents.

Suspending agents are needed in suspension compositions to provide a suspension in which the settling of the particles is impeded and at the same time remains sufficiently fluid to be syringeable. Exemplary suspending agents include, but are not limited to, sodium carboxymethylcellulose, povidone, polyvinylpyrrolidone compounds and polyethylene glycols. Preferred examples of polyethylene glycols are those having a molecular weight from about 300 to about 6000, e.g. polyethylene glycol 3350 and polyethylene glycol 4000. Preferred polyvinylpyrrolidone compounds according to the invention are those having a molecular weight from about 7000 to about 54000, for instance PVP K12, K17, K25 and K30, in particular K12 and K17, PVP K17 being the most preferred. Other suitable suspending agents include thickening or viscosity agents such as, for instance, well known cellulose derivatives, for example methylcellulose, carboxymethylcellulose, hydroxyethylcellulose and hydroxypropylmethylcellulose, gelatin and acacia, in particular methylcellulose.

The tonicity agents are used in suspension compositions to adjust the composition of the formulation to be within the desired isotonic range. Exemplary tonicity agents include, but are not limited to glycerin, mannitol, sorbitol, sodium chloride, and other electrolytes.

The buffering agents or pH-adjusting agent are used in suspension compositions to adjust the pH to a desirable range. Exemplary buffers are well known by those skilled in the art and include acetate, borate, carbonate, citrate, histidine, and phosphate buffers. While not intending to limit the scope of the invention in any way, certain compositions disclosed herein have a pH of from about 3.5 to about 7.0.

The preservatives in the suspension compositions are used to inhibit microbial growth. Suitable preservatives include, but are not limited to, hydrogen peroxide; sorbic acid; biquanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal and the like.

Heating is carried out for the length of time required to kill the pathogens of importance to the application in which the composition is used. Such a determination is well within the skill of a person of ordinary skill in the art. For example, in the compositions herein, the heating is maintained at or near the peak temperature for at least 15 to 60 minutes.

The particle size of methylprednisolone acetate in the suspension prepared according to the present invention ranges from about 0.1 μm to about 30 μm.

Figure 2:
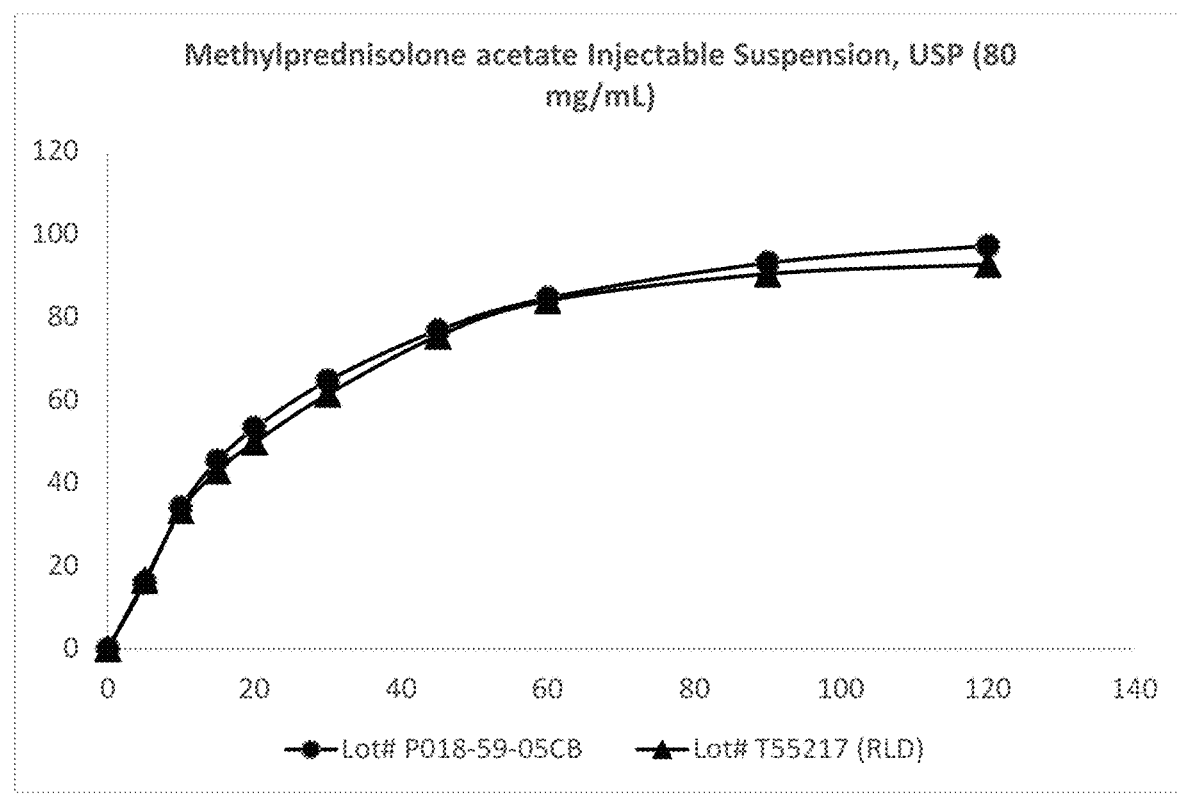
FIG. 2 is a dissolution profile comparison of Methylprednisolone Acetate Injectable Suspension, USP (80 mg/mL) with reference product (RLD).

The dissolution profile of methylprednisolone acetate suspension prepared according to the present invention is identical to the reference product. FIG. 2 shows the dissolution profile of a formulation prepared at a strength of 80 mg/mL with a marketed formulation at the same strength. The dissolution profile of a methylprednisolone acetate suspension prepared according to the present invention is compared with the reference product/marketed product using two factors: Difference Factor ($F_1$) and Similarity Factor ($F_2$).

$$f1 = \{[\Sigma t=1n|R-T|]/[\Sigma t=1nR]\} \times 100$$

$$f_2 = 50 \log\{[1+(1/n)\Sigma_{t=1}^{n}(R_t-T_t)^2]_{-0.5}*100\}$$

In the Similarity Factor equation, Rt and Tt are the cumulative percentage dissolved at each of the selected n time points of the reference and test products, respectively. The Difference Factor ($F_1$) is used to calculate the percent difference between the two curves at each time point and is a measurement of the relative error between the two curves. The Similarity Factor ($F_2$) measures the closeness between the two profiles. The Difference Factor ($F_1$) and Similarity Factor ($F_2$) are usually considered satisfactory if in the range of 0-15 and 50-100 respectively. The Difference Factor ($F_1$) and the Similarity Factor ($F_2$) values were found to be 5 and 71 respectively, confirming similarity between the marketed (reference) and developed (test) product.

The process for making a methylprednisolone acetate suspension according to the present invention is capable of (i) controlling the particle size of methylprednisolone acetate in a suspension to obtain a desired dissolution profile; (ii) making methylprednisolone acetate suspensions with variable particle size distributions by varying process parameters such as slurry volume and moist heat sterilization exposure time; and (iii) preventing the hydrolytic degradation of methylprednisolone acetate to methylprednisolone.

Without intending to be limited by theory, the inventors have developed the following theory as to how the process may protect multiple aspects of the methylprednisolone acetate, such as potency and particle size. Methylprednisolone acetate undergoes degradation by hydrolysis and oxidation when subjected to high temperatures in an aqueous medium. Water can act as an acid by formation of a hydronium ion ($H_3O^+$) and catalyze the cleavage of methylprednisolone acetate. Further, if there is dissolved oxygen in the water, the methylprednisolone acetate can be oxidized. The current process may reduce the degradation of methylprednisolone acetate by using a combination of one or more of: (a) limiting the slurry volume relative to the final product weight, e.g., keeping the slurry at between 30-40% w/w of the final product weight; (b) removing any dissolved oxygen from the water; (c) using a nitrogen atmosphere when applying moist heat sterilization; and (d) limiting the sterilization exposure to 15 minutes at 121° C.

The polysorbate 80 in the slurry sterically stabilizes the suspension products by preventing the formation of aggregates. During exposure of methylprednisolone acetate to moist heat some of the molecules may be solubilized at the high temperature and then during the cooling phase some of the molecules may form larger particles due to the combined effect of aggregation and Ostwald ripening phenomenon. The addition of polysorbate to the active ingredient slurry overcomes the effects of particle aggregation and Ostwald ripening during the moist heat sterilization.

The slurry may include 2-25% (w/w) methylprednisolone acetate and 0.001-0.5% (w/w) polysorbate. The slurry may include about 5-20% (w/w) methylprednisolone acetate and about 0.05-0.5% (w/w) polysorbate. The polysorbate may be polysorbate 80.

The heat sterilization of the slurry may be performed at a temperature of about 122° C., or over a range of about 115° C. to about 128° C.

It is to be understood that the above description is intended to be illustrative and not restrictive. Many embodiments will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

Example: Methylprednisolone Acetate Injectable Suspension Composition

| Sr. No | Ingredient | Quantity/mL | |
|---|---|---|---|
| | | 40 mg strength | 80 mg strength |
| 1 | Methylprednisolone acetate | 40 mg | 80 mg |
| 2 | Polyethylene glycol 3350 | 29.1 mg | 28.2 mg |
| 3 | Polysorbate 80 | 1.94 mg | 1.88 mg |
| 4 | Monobasic sodium phosphate | 6.8 mg | 6.59 mg |
| 5 | Dibasic sodium phosphate | 1.42 mg | 1.37 mg |
| 6 | Benzyl alcohol | 9.16 mg | 8.88 mg |
| 7 | Sodium chloride | 1.40 mg | 1.40 mg |
| 8 | Hydrochloric acid/Sodium hydroxide | q.s. for pH adjustment | q.s. for pH adjustment |
| 9 | Water for injection (WFI) | q.s. to 1 mL | q.s. to 1 mL |

Manufacturing Process:

The manufacturing process has the following steps:

Step I.

a) In Tank 1, dissolve polysorbate 80 in 30 kg water for injection.

b) Add required quantity of methylprednisolone acetate under stirring to form a slurry.

c) Make up the volume to 40 kg and mix under stirring for 2 hours.

d) Pass the slurry through an inline homogenizer connected to the tank for a period of about 30 minutes to break up any formed agglomerates. Keep the slurry under mixing throughout the compounding process.

e) Spurge with nitrogen to reduce dissolved and headspace oxygen level below 2 ppm.

f) Sterilize at 122° C. for 15 to 60 minutes under a nitrogen atmosphere.

g) Allow the solution to come to room temperature.

Step II.

a) In Tank 2, dispense 30 kg water and dissolve the formulation excipients in the following order: i) benzyl alcohol, ii) polyethylene glycol 3350, iii) monobasic sodium phosphate monohydrate, iv) dibasic sodium phosphate dihydrate, and v) sodium chloride.

b) Make up the weight to 40 kg with water for injection.

c) Filter the above solution through a 0.22 µm sterile filter into Tank 2 using an aseptic quick connect.

d) Rinse with additional water for injection sufficient to make the final batch weight and filter through a sterile filter into Tank 1.

Step III.

a) Transfer the product to a sterile holding tank (Tank 3).

The sterile suspension of methylprednisolone acetate is prepared as described in the Example. Analytical results of the formulation are summarized in Table 1.

TABLE 1

| Time (Months) | pH | | Methylprednisolone Acetate Assay (%) | | Benzyl Alcohol Assay (%) | | Total Impurity (%) | |
|---|---|---|---|---|---|---|---|---|
| | 25° C./ 60% RH | 40° C./ 75% RH | 25° C./ 60% RH | 40° C./ 75% RH | 25° C./ 60% RH | 40° C./ 75% RH | 25° C./ 60% RH | 40° C./ 75% RH |
| 0 | 6.09 | 6.09 | 101.2 | 101.2 | 101.5 | 101.5 | 0.185 | 0.185 |
| 1 | 6.06 | 6.08 | 100.9 | 104.6 | 99.8 | 097.5 | 0.091 | 0.127 |
| 2 | 6.05 | 6.07 | 106.3 | 104.8 | 99.9 | 101.0 | 0.210 | 0.258 |
| 3 | 6.02 | 6.03 | 101.7 | 106.8 | 99.8 | 98.1 | 0.231 | 0.254 |
| 6 | 5.98 | 6.08 | 100.2 | 99.7 | 100.4 | 99.5 | 0.231 | 0.277 |

The particle size of the methylprednisolone acetate in the suspension prepared according to the present invention compared with the reference product and the particle size distribution (PSD) results are summarized in Table 2.

TABLE 2

| PSD Range (μm) | Reference Product | Test Product (Present Invention) |
|---|---|---|
| $D_{10}$ | 1.59-1.81 | 1.77-2.77 |
| $D_{50}$ | 3.53-3.98 | 3.87-6.92 |
| $D_{90}$ | 7.14-7.79 | 7.93-17.30 |

It was observed from the above results that a methylprednisolone acetate suspension prepared in accordance to the present invention exhibited desirable characteristics in particle size of methylprednisolone acetate in suspension to obtain the desired dissolution profile and impurity profile within the specified limit.

The invention claimed is:

1. A sterile aqueous slurry consisting of methylprednisolone acetate, polysorbate 80 and water wherein the methylprednisolone acetate in the sterile aqueous slurry is in the form of particles having a $D_{90}$ of between 7.93 microns and 17.30 microns, a $D_{50}$ of between 3.87 microns and 6.92 microns, and a $D_{10}$ of between 1.77 microns and 2.77 microns, the concentration of methylprednisolone acetate in the slurry is about 80 mg/ml or about 160 mg/ml, and the concentration of polysorbate 80 in the slurry is about 3.88 mg/ml or about 3.76 mg/ml.

2. A sterile injectable suspension comprising the aqueous slurry of claim 1 and one or more pharmaceutically acceptable excipients selected from the group consisting of vehicle, suspending agent, surfactant, buffering agent, tonicity agent and preservative.

3. The sterile injectable suspension of claim 2, wherein the suspension comprises about 2% to about 8% methylprednisolone acetate, about 2.82% to about 2.95% polyethylene glycol 3350, about 0.18% to about 2% polysorbate 80 and one or more other pharmaceutically acceptable excipients.

4. The sterile injectable suspension of claim 2, wherein suspension pH is in the range of about 3.5 to about 7.0.

5. The sterile aqueous slurry of claim 1, wherein an application of moist heat sterilization to the slurry includes one or more of the steps of removing dissolved oxygen from the water, using a nitrogen atmosphere when applying the moist heat sterilization, and limiting the moist heat sterilization exposure to 15 minutes at 121° C.

6. The sterile injectable suspension of claim 2, wherein the aqueous slurry of methylprednisolone acetate and polysorbate comprises between about 30-40% w/w of the sterile injectable suspension.

7. The sterile injectable suspension of claim 2, wherein the suspension consists of:
 between about 40 to 80 mg/ml of methylprednisolone acetate;
 between about 28.2 to 29.1 mg/ml of polyethylene glycol 3350;
 between about 1.88 to 1.94 mg/ml of polysorbate 80;
 between about 6.59 to 6.8 mg/ml of monobasic sodium phosphate;
 between about 1.37 to 1.42 mg/ml of dibasic sodium phosphate;
 between about 8.88 to 9.16 mg/ml of benzyl alcohol;
 about 1.4 mg/ml of sodium chloride; and
 water to 1 ml.

8. A sterile aqueous slurry consisting of methylprednisolone acetate, polysorbate 80 and water wherein the methylprednisolone acetate in the sterile aqueous slurry is in the form of particles having a $D_{90}$ of between 7.93 microns and 17.30 microns, a $D_{50}$ of between 3.87 microns and 6.92 microns, and a $D_{10}$ of between 1.77 microns and 2.77 microns, the concentration of methylprednisolone acetate in the slurry is about 80 mg/ml or about 160 mg/ml, and the concentration of polysorbate 80 in the slurry is about 3.88 mg/ml or about 3.76 mg/ml, wherein the slurry is prepared in a process that includes the steps of:
 a) preparing an aqueous slurry of the methylprednisolone and polysorbate 80; and
 b) sterilizing the aqueous slurry by moist heat sterilization to form a sterile slurry, wherein the sterilization of the aqueous slurry is performed under homogenization and/or a nitrogen atmosphere and the moist heat sterilization comprises heating the aqueous slurry to a temperature of about 115° C. to about 128° C. for about 15 to 60 minutes.

9. The sterile aqueous slurry of claim 8, wherein the moist heat sterilization comprises heating the aqueous slurry to a temperature of about 122° C. for about 15 to 60 minutes.

10. A process for preparing the sterile injectable suspension of claim 2, the process comprising the steps of:
 a) preparing an aqueous slurry consisting of methylprednisolone acetate and polysorbate 80 in water; and
 b) sterilizing the aqueous slurry by moist heat sterilization to form a sterile slurry, wherein the potency of the methylprednisolone acetate in the suspension is not reduced by application of moist heat sterilization to the slurry.

11. The process of claim 10, further comprising:
 c) forming a solution of a mixture of one or more of a vehicle, a preservative, a suspending agent, a buffering agent, a tonicity agent and a surfactant;
 d) filtering the solution of step c) through a sterile filter; and
 e) combining the filtered solution of step d) with the sterile slurry of step b) to form a suspension.

12. The process of claim 10, wherein the sterilization of the aqueous slurry is performed under homogenization and/or a nitrogen atmosphere.

13. The process of claim 10, wherein the moist heat sterilization comprises heating the aqueous slurry to a temperature of about 115° C. to about 128° C. for about 15 to 60 minutes.

14. The process of claim 13, wherein the moist heat sterilization comprises heating the aqueous slurry to a temperature of about 122° C. for about 15 to 60 minutes.

* * * * *